United States Patent
Daval et al.

(10) Patent No.: US 10,123,547 B2
(45) Date of Patent: Nov. 13, 2018

(54) **SYNERGISTIC FERMENTATION OF *LACTOBACILLUS RHAMNOSUS* AND *LACTOBACILLUS PARACASEI* SUBSP *PARACASEI***

(75) Inventors: Christophe Daval, Choisy le Roi (FR); François Debru, Versailles (FR); Damien Lavergne, Sceaux (FR)

(73) Assignee: Compagnie Gervais Danone, Paris (FR)

( * ) Notice: Subject to any disclaimer, the term of this patent is extended or adjusted under 35 U.S.C. 154(b) by 480 days.

(21) Appl. No.: 13/696,939

(22) PCT Filed: May 11, 2011

(86) PCT No.: PCT/IB2011/052072
§ 371 (c)(1),
(2), (4) Date: Jan. 28, 2013

(87) PCT Pub. No.: WO2011/141881
PCT Pub. Date: Nov. 17, 2011

(65) Prior Publication Data
US 2013/0202738 A1   Aug. 8, 2013

(30) Foreign Application Priority Data

May 12, 2010   (WO) .................. PCT/IB2010/001400

(51) Int. Cl.
| | | |
|---|---|---|
| *A61K 35/66* | (2015.01) |
| *A23C 9/123* | (2006.01) |
| *C12N 1/20* | (2006.01) |
| *C12R 1/225* | (2006.01) |
| *A23L 33/135* | (2016.01) |
| *A61K 35/747* | (2015.01) |

(52) U.S. Cl.
CPC .......... *A23C 9/1234* (2013.01); *A23L 33/135* (2016.08); *C12N 1/20* (2013.01); *C12R 1/225* (2013.01); *A23V 2002/00* (2013.01); *A23Y 2220/73* (2013.01)

(58) Field of Classification Search
CPC . A23C 9/1234; A23L 1/3014; A23V 2002/00; C12R 1/225; C12N 1/20; A23Y 2220/73
See application file for complete search history.

(56) References Cited

FOREIGN PATENT DOCUMENTS

| | | |
|---|---|---|
| WO | 2005/095656 | 10/2005 |
| WO | 2010/043696 | 4/2010 |

OTHER PUBLICATIONS

Phillips, et al., Viability of Comerical Probioti Cultures in heddar Cheese, International Journal of Food Mirobiology, 108 (2006) 276-280.*
Lee, Comparison of Fermentative Capacities of Lactobacilli in Single and Mixed Culture in Industrial Media, Process Biochemistry, 40, pp. 1559-1564, 2005.

(Continued)

*Primary Examiner* — D. Lawrence Tarazano
*Assistant Examiner* — Philip A Dubois
(74) *Attorney, Agent, or Firm* — Morgan, Lewis & Bockius LLP

(57) ABSTRACT

The present invention relates to a process for preparing a fermented product by synergistic co-fermentation of *Lactobacillus rhamnosus* and *Lactobacillus paracasei* subsp. *paracasei*.

9 Claims, 3 Drawing Sheets

(56) References Cited

OTHER PUBLICATIONS

Figure 1:
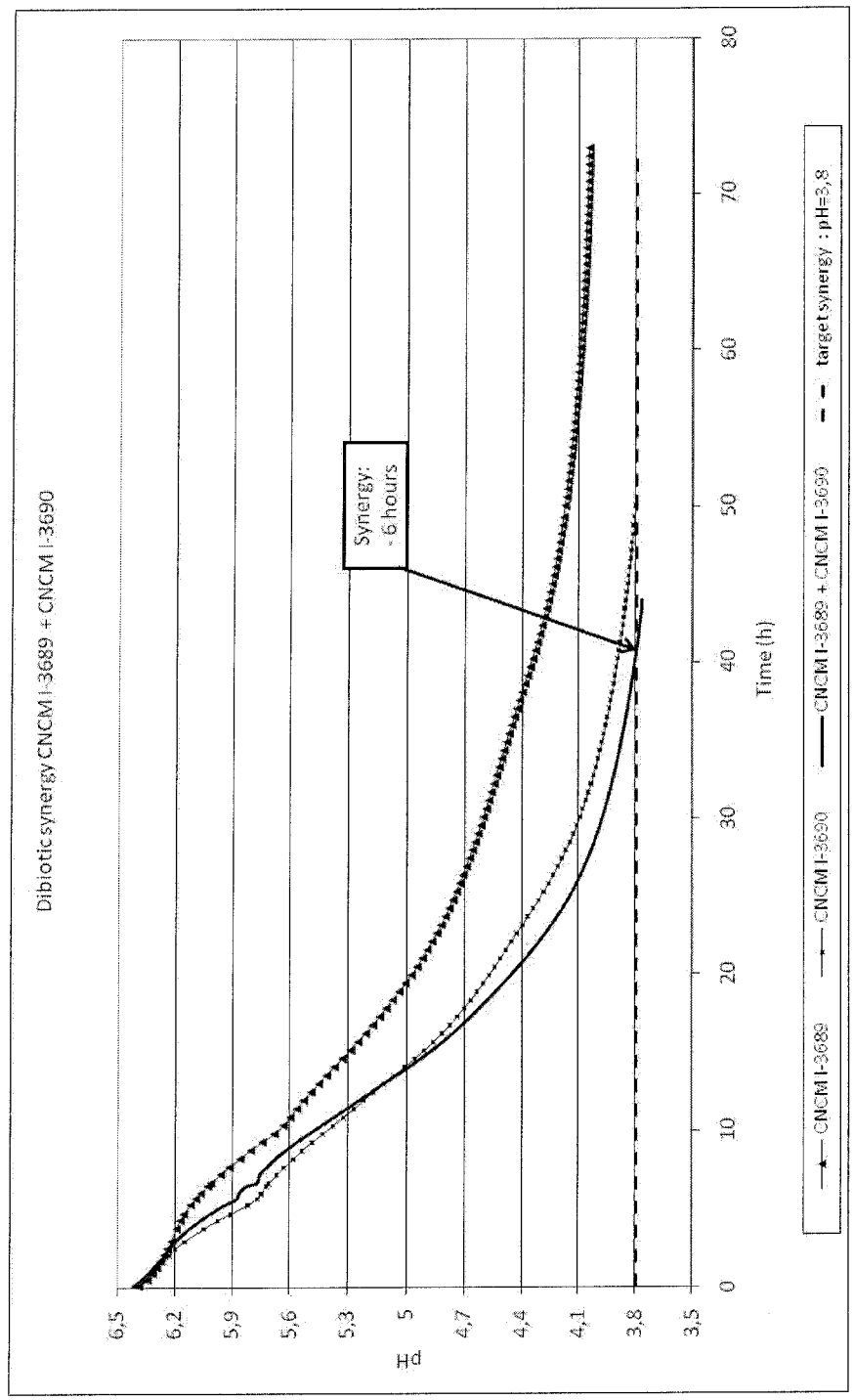

Verdenelli, Probiotic Properties of Lactobacillus Rhamnosus and Lactobacillus Paracasei Isolated From Human Faeces, Eur J Nurt, 48, pp. 355-363, 2009.

Timmerman, Monostrain, Multistrain and Multispecies Probiotics—A Comparison of Functionality and Efficacy, International Journal of Food Microbiology, 96, pp. 219-233, 2004.

Moussavi, An In Vitro Study on Bacterial Growth Interactions and Intestinal Epithelial Cell Adhesion Characteristics of Probiotic Combinations, Curr. Microbiol., 60, pp. 327-335, 2010.

Williams, Clinical Trial: A Multistrain Probiotic Preparation Significantly Reduces Symptoms of Irritable Bowel Syndrome in a Double-Blind Placebo-Controlled Study, Alimentary Pharmacology & Therapeutics, 29, pp. 97-103, 2001.

\* cited by examiner

SYNERGISTIC FERMENTATION OF *LACTOBACILLUS RHAMNOSUS* AND *LACTOBACILLUS PARACASEI* SUBSP *PARACASEI*

The invention relates to a fermentation method involving the synergistic growth of at least two *Lactobacillus* strains.

Fermentation methods by lactic acid bacteria have been developed for centuries. In lactic acid fermentation, the conversion by lactic bacteria of fermentable sugars into energy allowing bacterial growth results in the production of lactic acid. Fermentation by lactic acid bacteria is widely used for food processing.

For a long time health benefits have been assigned to some fermented food products such as yogurt, ranging from improved nutrient uptake/availability due to the fermentation, to specific effects assigned to the bacteria themselves.

More recently many clinical studies have been done to investigate the health benefits of some lactic acid producing strains. These strains are generally referred to as probiotics. According to the currently adopted definition by FAO/WHO, probiotics are: "Live microorganisms which when administered in adequate amounts confer a health benefit on the host". Most of the microorganisms used as probiotics are lactic acid bacteria, in particular strains from *Lactobacillus* and *Bifidobacteria* genus.

At first, probiotics were thought to beneficially affect the host mainly by improving its intestinal microbial balance, through competition with pathogens and toxin-producing bacteria. Today, specific health effects are being investigated and documented including alleviation of chronic intestinal inflammatory diseases, prevention and treatment of pathogen-induced diarrhea, urogenital infections, and atopic diseases. These effects have been attributed to the bacteria themselves, and also to the metabolites that they produce during fermentation.

Different studies are beginning to link different probiotic strains, even belonging to a same species, with different health benefits. For instance, since the human gut is home to some 400-500 types of microorganisms which can populate different areas of the digestive tract, it is thought that this diverse environment may benefit from multiple probiotic strains.

Research is therefore emerging on the additional health benefits of compositions containing multiple probiotic species or strains compared to those containing a single strain (TIMMERMAN et al., Int J Food Microbiol, 96, 219-33, 2004; WILLIAMS et al., Aliment Pharmacol Ther, 2008). WO2005095656 and VERDENELLI et al. (Eur J Nutr, 48, 355-63, 2009), describe a method for selecting probiotic strains, including a step of testing their adhesion properties to intestinal cells in the presence of other bacterial strains; these documents disclose more specifically two strains: *Lactobacillus rhamnosus* IMC 501 and *Lactobacillus paracasei* IMC 502 selected by this method, and propose to use them in co-administration for the improvement or restoration of the intestinal microflora Multiple strains probiotic compositions are classically obtained by growing separately each probiotic strain to be used in the composition under conditions suitable for the growth of said strain, and adding them to the final product after their growth is completed. Such process has the disadvantage of being time-consuming, and the need of using one fermentation vessel for each probiotic strain results in high production costs. Further, in most of cases, the probiotic strains are separated from their growth medium before being added to the final product. Therefore the metabolites that they release in the medium during their fermentation, and which may participate to the health benefit, are no longer present in the final product.

However, co-culturing several bacterial species or strains raises problems, due to the possible competition and/or interactions between these bacteria. For instance, if strains with a different growth rate are co-cultured, normally the fastest growing strain will overgrow the other. Also, the metabolites produced by each strain may have stimulatory effects or conversely inhibitory effects on one or more of the other strains of the co-culture.

The existence of either synergistic or antagonistic effects, during a fermentation, between bacteria used in classical food production is well-known. For instance, the classic "yogurt symbiosis" is a co-culture of *Streptococcus thermophilus* and *Lactobacillus bulgaricus*. The synergism between these two bacteria results in the acceleration of the multiplication of both of them, and of the acidification of the milk. Examples of the antagonistic effect of combinations of different bacteria can be found in the prior art (*E. coli* and *S. Thyphimurium*: TIMMERMAN et al., Int J Food Microbiol, 96, 219-33, 2004, *Aspergillus*: BUENO-DANTE et al, Journal of food protection, 69, 2544, October 2006), they involve the production of molecules like baceriocin, antibiotics and other metabolic products.

Currently, little is known about the interactions between species or strains of the genus *Lactobacillus*, and even less about *Lactobacillus* probiotics. It has been reported (LEE, Process Biochemistry, 40, 1559-64, 2005) that in the field of lactic acid production, mixed culturing of lactobacilli may be more effective than single culturing but to the applicant's best knowledge no description of a synergistic co-culture of bacteria of the subspecies *Lactobacillus casei/paracasei* and *Lactobacillus rhamnosus* has been reported. WO2005095656 and VERDENELLI et al. (Eur J Nutr, 48, 355-63, 2009) do not describe the co-culturing of the two strains *Lactobacillus rhamnosus* IMC 501 and *Lactobacillus paracasei* IMC 502.

The inventors have surprisingly found that when *Lactobacillus* strains of the species *paracasei* and *rhamnosus* are co-cultured in a dairy fermentation medium, a synergistic growth of these bacteria occurs. As a result, for a given fermentation time, the pH of the fermented medium is more acid, and/or the bacterial biomass in the co-culture is equal and generally higher than in mono-cultures of each individual strain.

The invention therefore provides a process for preparing a fermented dairy product containing two or more *Lactobacillus* strains, for instance, 3, 4, 5, 6, 7, 8, 9, or 10 *Lactobacillus* strains, wherein said process comprises:

a) inoculating a dairy fermentation medium with said *Lactobacillus* strains;

b) fermenting the inoculated medium by incubating it at a temperature suitable for growth of said strains, until it reaches a desired target pH or until the bacterial population reaches a desired target value;

c) stopping the fermentation and recovering the fermented product;

wherein the *Lactobacillus* strains are selected among strains of the species *Lactobacillus paracasei* subsp. *paracasei* and/or strains of the species *Lactobacillus rhamnosus*.

A dairy fermentation medium is herein defined as a milk-based liquid medium. Any animal or vegetal milk source could be considered. Cow milk is however preferred. It may be for instance whole, partially or fully skimmed milk, optionally reconstituted from powdered milk. It may also consist of a milk fraction, for instance whey, or mixtures of two or more of milk fractions. Preferably, said medium will be used without further supplementation. However, it may optionally be supplemented with ingredients such as sugars, starch, thickeners, etc, provided that these ingredients do not interfere with the growth of one or more of the co-cultured *Lactobacillus* strains, and provided that they are suitable for human or animal consumption. In particular, in case wherein one or more of the *Lactobacillus* strains cannot ferment lactose (for instance in the case of *Lactobacillus rhamnosus* LGG), a sugar which can be assimilated by said strain (for instance glucose) can be added to the dairy fermentation medium, preferably at a concentration of up to 10%, preferably of from 1% to 10%.

Said medium usually is sterilized before inoculation with the *Lactobacillus* strains. Sterilization is performed by classic methods known, such as heat treatment. The pH of the culture medium prior to inoculation with the bacteria is preferably from 5.5 to 7, preferably of about 6.5.

Any combination of strains of the species *Lactobacillus paracasei* subsp. *paracasei* and/or strains of the species *Lactobacillus rhamnosus* can be used for inoculating the medium.

For instance, one can use two or more strains of a single species, or combine one, two, or more strains of one of the species with one, two, or more strains of the other species. Generally, at least one of said strains has probiotic or potentially probiotic properties. Preferably, at least two, and still more preferably all of the strains used for inoculating the medium have probiotic or potentially probiotic properties.

Probiotic properties have been reported for strains found in both species *Lactobacillus paracasei* subsp. *paracasei* and *Lactobacillus rhamnosus*.

Examples of *Lactobacillus paracasei* subsp. *paracasei* strains with reported probiotic properties include:
  *Lactobacillus paracasei* subsp. *paracasei* CNCM I-1518, disclosed for instance in EP0794707;
  *Lactobacillus paracasei* subsp. *paracasei* CNCM I-3689, disclosed in WO2009122042;
  *Lactobacillus casei Shirota* (which actually belongs to the species *Lactobacillus paracasei* subsp. *paracasei*);

Examples of *Lactobacillus rhamnosus* strains with reported probiotic properties include:
  *Lactobacillus rhamnosus* CNCM I-3690, disclosed in WO2009130423
  *Lactobacillus rhamnosus* LGG (ATCC 53103), disclosed in U.S. Pat. No. 4,839,281
  *Lactobacillus rhamnosus* HN001, disclosed for instance in WO9910476.

Preferred strains combinations are those which include at least one, and preferably at least two of *Lactobacillus paracasei* subsp. *paracasei* CNCM I-1518, *Lactobacillus paracasei* subsp. *paracasei* CNCM I-3689, and *Lactobacillus rhamnosus* CNCM I-3690. For instance, they may include *Lactobacillus paracasei* subsp. *paracasei* CNCM I-1518 with *Lactobacillus paracasei* subsp. *paracasei* CNCM I-3689; *Lactobacillus paracasei* subsp. *paracasei* CNCM I-1518 with *Lactobacillus rhamnosus* CNCM I-3690; *Lactobacillus paracasei* subsp. *paracasei* CNCM I-3689 with *Lactobacillus rhamnosus* CNCM I-3690.

A particularly preferred strains combination includes the three strains *Lactobacillus paracasei* subsp. *paracasei* CNCM I-1518, *Lactobacillus paracasei* subsp. *paracasei* CNCM I-3689, and *Lactobacillus rhamnosus* CNCM I-3690.

These combinations may further include other probiotic or non-probiotic strains of *Lactobacillus paracasei* subsp. *paracasei* and/or *Lactobacillus rhamnosus*.

Generally, the *Lactobacillus* strains are inoculated in the dairy fermentation medium in a global quantity of at least $10^6$ CFU/ml, preferably of from $5\times10^6$ to $1\times10^8$ CFU/ml, more preferably of from $1\times10^7$ to $5\times10^7$ CFU/ml, and still more preferably of about $2\times10^7$ CFU/ml.

The proportion of each strain in the global population of *Lactobacillus* inoculated will be chosen in function of the proportion that one wishes to obtain in the final fermented product. Typically, each individual strain should represent at least 1% of the global population inoculated. It may therefore represent up to 99% in the case of a two-strains co-culture, up to 98% in the case of a three-strains co-culture, and so on. Preferably, each individual strain will represent at least 5%, more preferably at least 10% of the global population.

The individual strains may be inoculated separately, or mixed together prior to inoculation.

After inoculation of the dairy medium, fermentation is conducted under the usual conditions suitable for growth of the inoculated bacterial strains.

Both *Lactobacillus paracasei* subsp. *paracasei* and *Lactobacillus rhamnosus* are mesophilic bacteria. Therefore, the fermentation temperature will be generally of from 30° C. to 42° C., preferably of from 34° C. to 38° C., most preferably of about 37° C.

The fermentation is stopped when the fermentation medium reaches the desired target pH or when the global *Lactobacillus* population reaches the desired target value.

Generally, the target pH will be of from 3.7 to 4.2, preferably of from 3.75 to 3.9, most preferably of about 3.8.

The target value for the global *Lactobacillus* population is generally of at least 5 times, preferably of at least 10 times, still more preferably of at least 100 times, and usually up to 1000 times the population inoculated. Generally, the fermentation is stopped when the bacterial population is of at least $10^8$ CFU/ml, preferably of at least $10^9$ CFU/ml.

The fermentation time for reaching the target pH or the target *Lactobacillus* population depends on the fermentation conditions (including in particular the size of the inoculated population, the composition of the dairy fermentation medium, and/or the fermentation temperature). When using a combination of *Lactobacillus paracasei* subsp. *paracasei* and/or *Lactobacillus rhamnosus* strains, the fermentation time is shorter. It can be for example of at least 1% shorter, preferably of at least 5% shorter, preferably of at least 10% shorter, for example of from 1% to 80% or of from 5% to 50%, or of from 10 to 40% shorter than the fermentation time needed for reaching the same target pH or the same target *Lactobacillus* population with a *Lactobacillus paracasei* subsp. *paracasei* or *Lactobacillus rhamnosus* strain cultivated individually under the same fermentation conditions. A fermentation time shorter of 1% to 10% is considered as a slight synergy. A fermentation time shorter of at least 10% is considered as a high synergy.

Generally, the fermentation conditions will be chosen so as the fermentation time is of from 10 to 120 hours, preferably 25 to 75 hours, and preferably so as the fermentation time does not exceed 50 hours.

The invention also encompasses a fermented dairy product obtainable by the process of the invention. This product usually contains, in addition to the *Lactobacillus paracasei* subsp. *paracasei* or *Lactobacillus rhamnosus*, strains used for the fermentation, the fermented dairy medium. Therefore, it contains all the metabolites produced by the strains during the fermentation, including the metabolites resulting from the interactions between the co-cultured strains (for instance the metabolites released by one of the strains, which have been further metabolised by another strain).

This fermented dairy product can be used as such, in particular as a food product, or a nutritional supplement.

It can also be added to a food product, in particular a dairy product such as a yogurt, or to a nutritional, pharmaceutical, or cosmetic composition. The food composition, as well as the nutritional, pharmaceutical, or cosmetic compositions comprising said fermented dairy product are also part of the invention.

The present invention is further illustrated by the additional description which follows, which refers to non-limiting examples of the implementation of the process of the invention.

EXAMPLE 1. SYNERGISTIC GROWTH OF TWO OR THREE *LACTOBACILLUS* STRAINS

Material and Methods:
1) Strains:
The following strains were studied:
*Lactobacillus rhamnosus* strains:
Rhamno A
Rhamno B
HN001
CNCM I-3690
*Lactobacillus paracasei* subsp. *paracasei* strains
Paracasei A
Paracasei B
CNCM I-1518
CNCM I-3689

HN001, CNCM I-3690, CNCM I-1518 and CNCM I-3689 are known probiotic strains, while Rhamno A, Rhamno B, Paracasei A and Paracasei B are ordinary strains chosen at random.

2) Cryotubes:
The strains were conserved in cryotubes (2 ml) which were previously made up according to the protocol below.

Strain culture was performed with Man Rogosa Sharpe (MRS) broth and incubated 16 h at 37° C.; sterilized DMSO (5.3%) has been added to improve the strain stability during the storage phase. The cryotube was frozen with nitrogen steam during 30 nm. The strain purity was checked with API gallery 50CH+methylen blue. The cryotubes were stored at −80° C.

3) Subculture with Growth Medium:
Each strain was cultured individually. The cryotubes were defrosted under sterile conditions and 1 ml (1%) of culture was added to 100 ml of sterile MRS broth used as growth medium, and incubated at 37° C. until the culture reaches the stationary phase (pH around 4.00). The subculture was centrifuged at 5000 rpm during 15 nm at 4° C. Supernatant was replaced by sterile tryptone salt.

4) Fermentation in Dairy Medium:
The dairy medium contains skimmed milk powder (120 g) and distilled water (930 g). After 1 h rehydratation, the mix was sterilized by autoclaving for 15 nm at 115° C.

The bacteria from the subcultures were inoculated at a global bacterial population of $2 \times 10^7$ cell/ml in 200 ml of dairy medium. When 2 strains were used, each strain represented ½ of the global bacterial population; when 3 strains were used, each strain represented ⅓ of the bacterial population. Fermentation was conducted at 37° C., and monitored by measuring the decrease of pH in the culture medium. Fermentation was stopped when a target pH of 3.80 was reached.

The cell count analysis is performed by serial dilutions of the fermented medium with tryptone salt solution, and plating on Petri dishes with MRS agar. Petri dishes are incubated at 37° C. during 72 H in anaerobic conditions.

Figure 2:
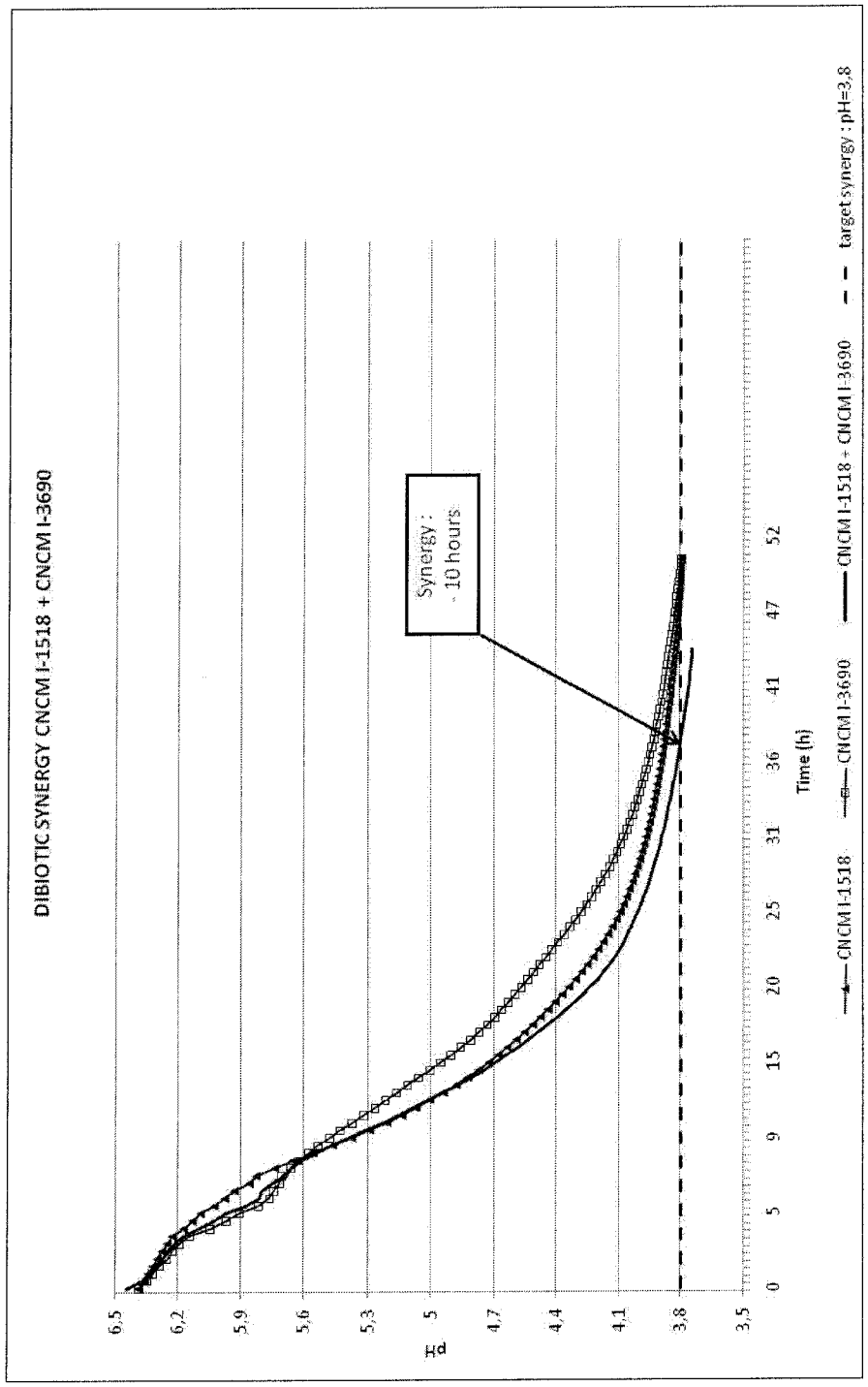
Figure 3:
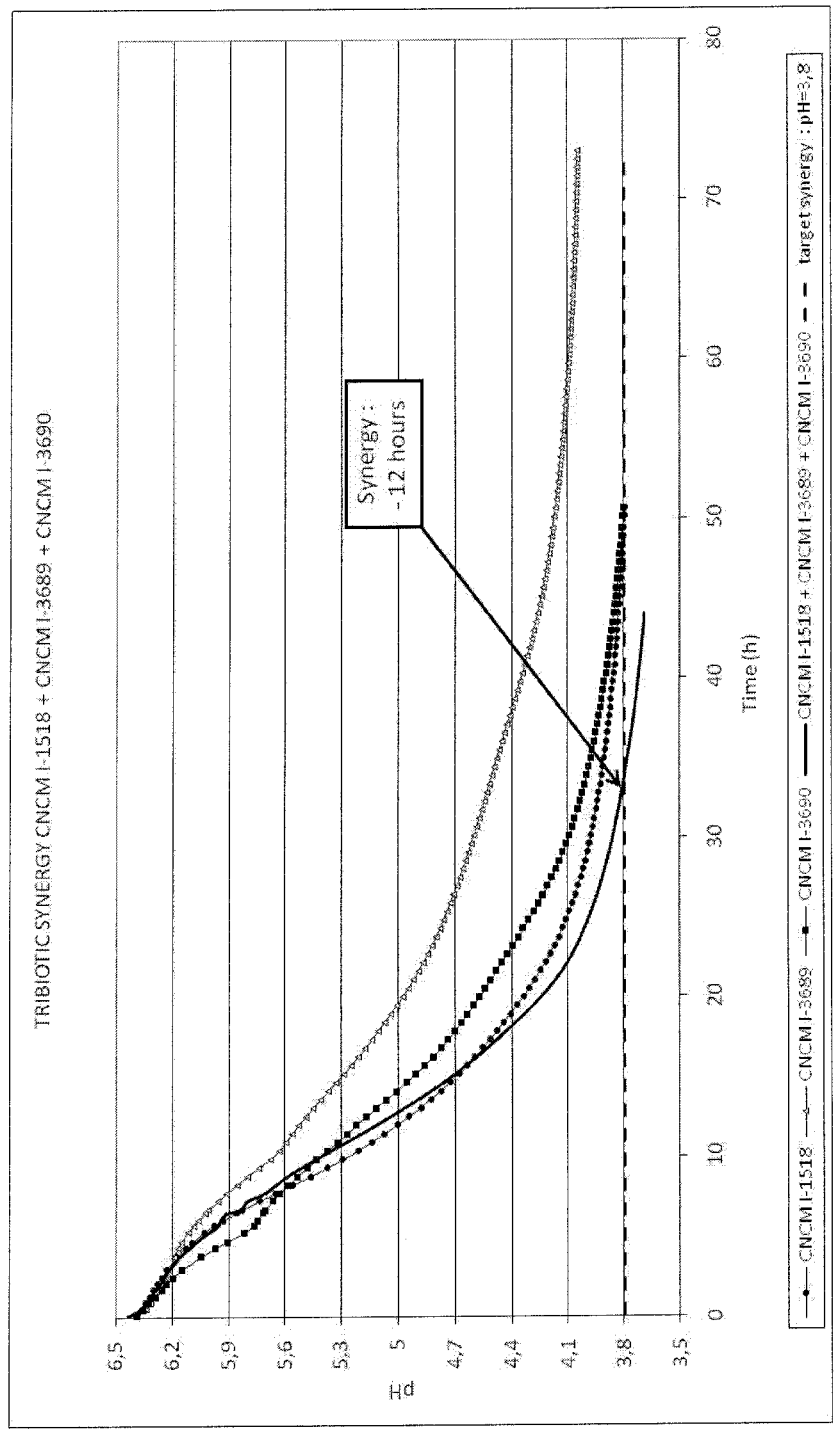

Results:

The results are shown in Tables I and II and FIGS. 1 to 3

Table I shows the total bacterial count when target of pH 3.80 is reached.

Table II shows the decrease in fermentation time needed to reach the target pH of 3.80 (average of 2 independent experiments). The decrease is calculated by the difference between the time necessary to reach pH=3.80 for the strain which shows the fastest fermentation rate when cultivated alone, and the time to reach pH=3.80 for the strain combination. We consider that a synergistic effect is present when the fermentation time reduction with combination is of at least 1%, preferably with at least the same minimum level of population.

TABLE I

| N° of combination | Strain combination | Total count CFU/g |
|---|---|---|
| 1 | CNCM I-1518 + CNCM I-3689 | 3 × 10e9 |
| 2 | CNCM I-1518 + Paracasei B | 3 × 10e9 |
| 3 | CNCM I-1518 + Rhamno A | 2.8 × 10e9 |
| 4 | CNCM I-1518 + HN001 | 3 × 10e9 |
| 5 | CNCM I-3689 + CNCM I-3690 | 3.1 × 10e9 |
| 6 | CNCM I-1518 + Paracasei A | 4 × 10e9 |
| 7 | CNCM I-1518 + CNCM I-3690 | 3.1 × 10e9 |
| 8 | CNCM I-1518 + CNCM I-3689 + Rhamno B | 4 × 10e9 |
| 9 | CNCM I-1518 + CNCM I-3689 + Rhamno A | 2.5 × 10e9 |
| 10 | CNCM I-1518 + CNCM I-3689 + HN001 | 1.4 × 10e9 |
| 11 | CNCM I-1518 + CNCM I-3690 + CNCM I-3689 | 3 × 10e9 |
| 12 | CNCM I-1518 + Paracasei B + CNCM I-3690 | 2.75 × 10e9 |
| 13 | CNCM I-1518 + Paracasei A + CNCM I-3690 | 3.2 × 10e9 |

Table I, shows total count results. The target count (same as for the fermentation of each individual strain=at least 1×10e9 CFU/g) is obtained for each combination tested in Table II.

TABLE II

| N° of combination | Strain combination | Decrease in fermentation time (average of 2 independent experiments) | Decrease in fermentation time (%) |
|---|---|---|---|
| 1 | CNCM I-1518 + CNCM I-3689 | −1 hr | −1% |
| 2 | CNCM I-1518 + Paracasei B | −1 hr | −1% |
| 3 | CNCM I-1518 + Rhamno A | −4 hrs | −10% |
| 4 | CNCM I-1518 + HN001 | −6 hrs | −13% |
| 5 | CNCM I-3689 + CNCM I-3690 | −6 hrs | −12% |
| 6 | CNCM I-1518 + Paracasei A | −7 hrs | −15% |
| 7 | CNCM I-1518 + CNCM I-3690 | −10 hrs | −19% |

TABLE II-continued

| N° of combination | Strain combination | Decrease in fermentation time (average of 2 independent experiments) | Decrease in fermentation time (%) |
|---|---|---|---|
| 8 | CNCM I-1518 + CNCM I-3689 + Rhamno B | −4 hrs | −12% |
| 9 | CNCM I-1518 + CNCM I-3689 + Rhamno A | −6 hrs | −15% |
| 10 | CNCM I-1518 + CNCM I-3689 + HN001 | −7 hrs | −16% |
| 11 | CNCM I-1518 + CNCM I-3690 + CNCM I-3689 | −12 hrs | −29% |
| 12 | CNCM I-1518 + Paracasei B + CNCM I-3690 | −14 hrs | −28% |
| 13 | CNCM I-1518 + Paracasei A + CNCM I-3690 | −20 hrs | −40% |

Table II clearly demonstrates that all the combinations of *L. rhamnosus* and/or *L. casei* give an unexpected synergistic increase in growth, reflected by a decrease in fermentation time of at least 1 hour. This synergistic effect is even stronger when three strains are co-fermented.

FIG. 1 shows the fermentation curves under the same culture conditions, of the 2 individual strains CNCM I-3689 and CNCM I-3690 and of the 2 strains in co-culture (combination 5). The co-fermentation results in a decrease of 6 hours in the fermentation time.

FIG. 2 shows the fermentation curves under the same culture conditions, of the 2 individual strains CNCM I-1518 and CNCM I-3690 and of the 2 strains in co-culture (combination 7). The co-fermentation results in a decrease of 10 hours in the fermentation time.

FIG. 3 shows the fermentation curves under the same culture conditions, of the 3 individual strains CNCM I-1518, CNCM I-3689, and CNCM I-3690 and of the 3 strains in co-culture (combination 11). The co-fermentation results in a decrease of 12 hours in the fermentation time.

These results confirm those presented in Table II, showing a synergistic effect of the co-fermentation of strains on the growth rate, and that the combination of three different strains is the most effective in shortening the fermentation time.

The invention claimed is:

1. A process of preparing a fermented dairy product comprising two *Lactobacillus* strains, wherein said process comprises:
   (a) inoculating a dairy fermentation medium with *Lactobacillus paracasei* subsp. *paracasei* deposited with the Collection Nationale de Cultures de Micro-organisms (CNCM) under accession number 1-1518 and *Lactobacillus rhamnosus* deposited with the CNCM under the accession number 1-3690;
   (b) fermenting the inoculated medium by incubating it at a temperature suitable for growth of said strains, until it reaches a desired target pH or until the global *Lactobacillus* population reaches a desired target value; and
   (c) stopping the fermentation and recovering the fermented product wherein the fermentation is stopped when the global *Lactobacillus* population is of at least 10 times the population inoculated.

2. The process of claim 1, wherein the *Lactobacillus* strains are inoculated in the dairy fermentation medium in a global quantity of at least $10^6$ CFU/ml.

3. The process of claim 1, wherein each individual strain is at least 1% of the global population of inoculated *Lactobacillus*.

4. The process of claim 1, wherein the fermentation is conducted at a temperature of from 30° C. to 42° C.

5. The process of claim 1, wherein the fermentation is stopped when a target pH of from 3.7 to 4.2 is reached.

6. The process of claim 1, wherein the fermentation is stopped when the global *Lactobacillus* population is of at least $10^8$ CFU/ml.

7. The process of claim 1, wherein the global *Lactobacillus* population in the recovered fermented product is of from $10^6$ to $10^9$ CFU/ml.

8. The process of claim 1, wherein the fermented dairy product further comprises *Lactobacillus paracasei* subsp. *paracasei* deposited with the CNCM under the accession number 1-3689.

9. The process of claim 1, wherein the fermentation is stopped when the global *Lactobacillus* population is of at least 100 times the population inoculated.

* * * * *